United States Patent [19]

Shetty

[11] 4,113,857

[45] Sep. 12, 1978

[54] PROCESS FOR THE PREPARATION OF IODOPHOR COMPOUNDS AND METHODS FOR STABILIZING IODOPHOR PHARMACEUTICAL COMPOSITIONS CONTAINING THE SAME

[75] Inventor: Bola Vithal Shetty, Stamford, Conn.

[73] Assignee: The Purdue Frederick Company, Norwalk, Conn.

[21] Appl. No.: 797,094

[22] Filed: May 16, 1977

[51] Int. Cl.$^2$ .............................................. A61K 33/18
[52] U.S. Cl. .................................... 424/150; 252/106; 424/80
[58] Field of Search ......................... 424/150; 252/106

[56] References Cited

U.S. PATENT DOCUMENTS

| | | | |
|---|---|---|---|
| 3,028,300 | 4/1962 | Cantor et al. | 424/150 |
| 3,039,916 | 6/1962 | Neracher et al. | 424/150 |
| 3,644,650 | 2/1972 | Sabatelli et al. | 424/150 |

OTHER PUBLICATIONS

Chemical Abstracts, vol. 59, (1963), p. 1266e.

*Primary Examiner*—V. D. Turner
*Attorney, Agent, or Firm*—Steinberg & Blake

[57] ABSTRACT

An improved process for preparing iodophor preparations which comprises adding an ion selected from the group consisting of iodate, bromate, chlorite, chromate, hypochlorite, permanganate and persulfate ions and hydrogen peroxide to the iodine carrier selected from the group consisting of povidone, cationic, anionic and nonionic detergent compounds and an iodide salt, to result in a substantially pure iodophor compound which is virtually free of autodegraded iodide ion contamination and unreacted elemental iodine, said iodophor compounds exhibiting an enhanced stability. The process is also applicable to eliminate the presence of elemental iodine contaminants, iodide contamination and loss of titratable iodine during the process preparing pharmaceutical dosage forms containing iodophor active ingredients to enhance the stability and potency of the respective product.

14 Claims, No Drawings

PROCESS FOR THE PREPARATION OF IODOPHOR COMPOUNDS AND METHODS FOR STABILIZING IODOPHOR PHARMACEUTICAL COMPOSITIONS CONTAINING THE SAME

THE STATE OF THE ART

Iodophor compounds are well known germicidal agents comprising the combination of iodine with an organic carrier selected from the group consisting of povidone, and cationic, anionic and non-ionic detergents. All of the iodophor preparations hitherto known are prepared by the direct combination of elemental iodine and the carrier and the limitations of this process are well known to the art. (See for example, U.S. Pat. Nos., 2,706,701; 2,826,532; 3,039,916; 2,860,080; 2,840,510; 2,759,869, and others.

All of the commercially available iodophor pharmaceutical preparations have an inherent limitation of a sharp fall in titratable iodine content with subsequent loss in germicidal potency on standing. While many methods have been directed to obtain a substantially pure, stable iodophor product, all products hitherto known in the art possess variable quantities of iodides with act to dissolve unreacted elemental iodine as well as to serve as a catalyst for further autodegradation of the iodophor compound. This degradation of the iodophor compound and loss in titratable iodine content results in a lowered potency of pharmaceutical dosage forms containing these compounds and thereby limits the use of these agents for germicidal use.

This invention relates to an improved process for preparing an adduct of iodine with a polymeric or a non-polymeric organic halogen carrier to form an iodophor compound which is virtually free of iodide ion contamination; a method to avoid the formation of iodide contaminants both during the process of iodophor manufacture as well as during their use in aqueous and/or aqueous organic solvents, and to provide a method for an improved stabilization of both an iodophor compound and pharmaceutical compositions containing the same. In particular, it is concerned with an improved method for the manufacture of povidone-iodine, cationic and anionic and non-ionic detergent iodophor compounds and compositions containing the same which are virtually free of iodide contaminants and which exhibit an improved stability and reduced toxicity.

Moreover, a method is provided to reduce and/or avoid the formation of iodide ions as a result of reduction of the active titratable iodine moiety of an iodophor, either upon aging or when dissolved in a polar solvent such as water or hydro-organic solvent mixtures during the manufacture of pharmaceutical dosage forms. Still another object of this invention is to provide a method for increasing the stability of formed iodophor preparations so that their iodine content does not decay and their germicidal potency is uniformly maintained for extended periods of time without the necessity to add excess amounts of active ingredients.

Iodine has long been recognized to be an excellent germicide but because of its inherent chemical and physical limitations its use as an antiseptic degerming agent has been limited. Elemental iodine has a high vapor pressure which causes great loss in germicidal potency as the iodine content volatizes from antiseptic preparations containing iodine as the antimicrobial agent. Moreover, because of this high vapor pressure, germicidal iodine preparations cannot be bandaged since corrosive destruction of skin occurs.

Iodine is virtually insoluble in water with a solubility of 0.096 parts of iodine per 100 parts of water at 60° C and therefore germicidally active aqueous iodine solutions cannot be prepared requiring alcohol or other irritating solvents. It is known that aqueous solutions of iodine may be prepared through the use of inorganic iodides as a solubilizing aid but these deep brown-colored solutions are extremely corrosive to both animate and inanimate substances. Moreover, all elemental iodine preparations stain skin and natural fibers.

There have been many efforts described in the art to preserve the germicidal properties of iodine and at the same time reduce its noxious corrosive properties and its high vapor pressure, so that it may be used safely and effectively for both the prophylaxis and treatment of infection in humans and animals.

The first advance in achieving this goal was through the formation of a novel complex compound between polyvinylpyrrolidone and iodine, which gave rise to a new class of compounds known as iodophors. The complex compound of polyvinylpyrrolidine and iodine, also known as povidone-iodine, dramatically reduced the noxious toxic properties of elemental iodine all the while preserving the broad germicidal spectrum of elemental iodine and its use while in therapy is well known.

Since the advent of povidone-iodine, other iodophor compositions comprising complex adducts and mixtures of iodine with organic polymeric compounds, as for example, surface-active agents of both the non-ionic and anionic classes were introduced, each compound or agent claiming to result in a reduction of the destructive and corrosive properties of elemental iodine which have limited its use in combating infections of humans and animals. However, despite the marked advances in the reduction of the noxious untoward and toxic properties of elemental iodine achieved by the class of iodophor compounds, the literature continues to report side-reactions which may be attributed to the presence of free elemental iodine in solution.

It is important to recognize that a common contaminant of the entire class of iodophor preparations is the iodide ion and to recall the well known property of the iodide ion to facilitate the dissolution of elemental iodine in water. Thus, it may be shown that iodides which are formed during the course of the manufacture of a respective iodophor compound or when an iodophor compound is dissolved in water, the iodide content occurs from a reduction of the available iodine present in the compound or when released in solution to exert the germicidal action. The iodide ion in turn acts as a solubilizing aid for either the poorly reacted or unreacted iodine present in the product and thereby results in free corrosive elemental iodine which may result in the reported injuries.

The basic method to prepare an iodophor compound is essentially that of bringing into intimate contact elemental iodine with a selected polymeric carrier whether it be polyvinylpyrrolidone, an anionic surface active agent or a nonionic surface active agent. The surface active agents usually used to form iodophor compounds comprise polymeric compounds of different molecular weights. The class of organic iodophor compounds consist of two distinct groups; the first, that of polyvinylpyrrolidone-iodine which is a non-detergent, non-surface active polymer-iodine compound and the second group comprising a variety of detergent-surface active compounds and iodine.

In preparing the iodophor compound, the elemental iodine of the polymeric carrier are mixed either in the dry form or in the presence of a suitable solvent. When the iodophor is prepared in the dry state, the intimate mixing may be achieved by grinding the iodine and the polymer compound in a suitable mechanical mixer for a specified period of time. The completeness of reaction depending upon the duration of the contact between the reacting substances, there being sufficient moisture both in the atmosphere and the polymer reagent, to permit the necessary chemical reaction to occur.

Upon completion of reaction, there is obtained an iodophor compound which contains the polymeric carrier and iodine in reproducible proportions of one to the other. The iodine is present in three forms, as available or titratable iodine, iodide ion and bound iodine. The distinction between these forms is readily assessible on an analytical basis. The available or titratable iodine is determined by dissolving a known weight of the product in water and titrating the solution with 0.1N sodium thiosulfate solution using starch as an indicator.

The amount of iodine present as the iodide ion, is determined by dissolving a known weight of the polymeric compound in water and adding sodium bisulfite test solution until the brown color disappears. The solution is then acidified with nitric acid and a calculated volume of 0.1N silver nitrate, test solution, is added. The excess silver nitrate test solution is then titrated with 0.1N ammonium thiocyanate test solution using ferric ammonium sulfate as the indicator. Each milliliter of 0.1N silver nitrate is equivalent to 12.69 miligrams of iodine. The iodide ion concentration is calculated as the difference between the result of the iodine concentration obtained by ammonium thiocyanate titration and the amount of titratable iodine determined by sodium thiosulfate titration.

To determine the amount of bound iodine, the total iodine concentration is determined by combustion methods, such as are well known in the art as for example that described by Hallet in Scott's, Standard Methods of Chemical Analysis and the amount of bound iodine is determined by subtracting the quantity of titratable iodine and the quantity of iodine ion from the total iodine content determined by combustion. Thus, each of the known iodophor products may be shown to contain a variable quantity of iodide ion which acts as a cosolvent for unreacted and/or loosely-bound elemental iodine, to result in potential toxic reactions, when an iodophor is used to prepare a pharmaceutical preparation.

It is known that when an iodophor compound is dissolved in aqueous or hydro-organic solvent, the level of titratable iodine will gradually decrease in the course of time, and that there will be an increase in the acidity of the iodophor solution. This lowering in titratable iodine content is the result of the well known reaction whereby the titratable iodine in aqueous solution reacts with hydrogen ions to form hydriodic acid which is a source for the iodide ion. Thus, there is a catalytic conversion of available germicidal iodine to iodide ion over the course of time to result in a loss of germicidal potency as well as to increase the solubilization of elemental iodine in its free form thereby increasing the potential for toxicity.

While the loss of a germicidal potency with time through the conversion of titratable iodine to the iodide ion may be compensated by adding an excess of the iodophor compound at the time of manufacture of the pharmaceutical preparation so as to constantly maintain a high level of titratable active germicidal iodine, this practice is costly as well as inherently contributory to a further increase of dissolved unreacted or loosely-bound elemental iodine in the solution to contribute possible noxious toxic responses.

An important object of this invention is to provide a new process for the preparation of an iodophor compound which is substantially free of iodide ion and at the same time avoids the occurence of unreacted iodine and/or loosely-bound iodine as a by-product of the process of manufacture. Another object of this invention is the provision for an aqueous solution of an iodophor which does not exhibit a loss in available iodine content by its conversion into iodide ion on aging and thereby possesses an improved stability profile. This improved stability eliminates the need to use an excess quantity of active iodophor ingredient in the manufacture of pharmaceutical products thereby not only effecting a great savings in cost but also avoiding the increase in solubility of additional elemental iodine as would be contained in the excess active ingredient and to reverse the reactions known to occur to convert iodine to iodide.

Polyvinylpyrrolidine-iodine (povidone-iodine) is a complex iodophor compound, and is commercially available to contain not less than 9 percent and not more than 12 percent of titratable iodine, although povidone-iodine compounds containing 30 percent of titratable iodine are known, as are povidoneiodine compounds containing 30 percent of titratable iodine are known, as are povidone-iodine compounds containing less than 9 percent of titratable iodine. When an anionic or nonionic detergent iodine complex is considered, these iodophors have been shown to contain as high as 30 percent titratabable iodine and as low as 5 percent titratable iodine. It is important to recognize that the specific ratio of polymeric carrier and iodine is determined by the fixed proportions of reagents used in the synthesis; the molecular weight of the polymer selected and the reaction conditions and time of reaction utilized.

Notwithstanding the above synthetic variables, the resultant product obtained from a given method of synthesis, is homogeneous and reproducible and contains the calculated proportion of iodine to polymeric carrier as set forth by the synthetic protocol selected in accord with the above variables. The only variable common to all these methods is the concentration of iodide ion contained in the formed product; the amount of unreacted elemental iodine present in the product, and the behavior of the formed iodophor compound in solution with regard to the rate of conversion of available iodine to iodide content and consequent fall in potency.

It has been found that when an amount of from 0.005 percent to 1.0 percent by weight of iodate ion is added to a selected quantity of povidone-iodine at the time of its manufacture there is obtained a polymeric iodophor compound that is uniquely free of iodide ion content and exhibits a preferred stability in aqueous solution so that the fall in the amount of titratable iodine on aging is greatly reduced whereby no excess quantity of iodophor is necessary in the manufacture of pharmaceutical preparations employing said iodophor product. Thus, for example, if it is desired to prepare povidone-iodine containing 10 percent titratable iodine and which is to be virtually free of iodide ion, this may be accomplished by combining 90 parts by weight of povidone with 10 parts by weight of iodine in the presence of 0.05 percenty by weight of potassium iodate. The dried powders are intimately mixed in a ball-mill for a period of at least four hours to obtain the desired compound, polyvinylpyrrolidone iodine, containing 10 percent by weight of titratable iodine with virtually no iodide ion.

Should it be desired to prepare povidone-iodine in solution, then the appropriate quantity of povidone is dissolved in a sufficient quantity of distilled water and the appropriate quantity of iodine added. To this is added a quantity of potassium iodate of from 0.01 percent to 0.1 percent, depending on the amount of iodine used as a reagent, which may range from 8 to 12 percent by weight and; the resultant solution is then evaporated to obtain povidone-iodine, substantially free from iodide ion and which possesses a unique stability.

It was further found that iodophors in general and povidone-iodine in particular, may be prepared by adding from 0.05 percent to 1.0 percent of a water soluble iodate salt to an acidified aqueous solution of the polymeric iodine carrier and a sufficient quantity of a water soluble iodide salt, as for example, ammonium, sodium, potassium or lithium iodides, said iodide salt being present in sufficient quantity to provide the desired concentration of iodine in the course of the reaction to form the desired iodophor compound. The mixture is stirred and may be warmed, although this is not critical until the iodide content is no longer determinable upon assay. The resultant brown colored solution is then concentrated to dryness to result in a substantially pure iodophor compound containing a predetermined ratio of iodine to polymeric carrier. It may be necessary in the course of the reaction to add additional iodate ion and further acid as the monitoring of the pH of the reaction required so that it is on the acid side through the reaction period. The iodophors formed as a result of this reaction corresponds in every respect to the commercially available described products in the literature, but is unique in that it is free of chloroform extractable unreacted ione and is virtually without iodide content. The shelf-like stability of the iodophor compound obtained by the method set forth above is superior to the shelf-like stability of commercially available povidone-iodine and furthermore no excess amount of active ingredient is required to prepare a pharmaceutical dosage form. Although the shelf-life stability is materially improved for the povidone-iodine product described herein so that no excesses are required, there is no modification of the observed microbicidal potency of the preparations prepared therefrom. Dosage forms prepared with the formed povidone-iodine according to the present method retains their broad spectrum antimicrobial potency throughout their entire shelf-life as is demonstrated through testing and are superior to the preparations prepared with iodophors obtained by the older methods.

It was further found the method of forming an iodophor may be applied to the preparation of other iodophor complexes comprising non-ionic, cationic and anionic detergent carriers. An iodophor compound prepared with a commercially available non-ionic surface active agent as for example, the liquid non-ionic polyglycol ether type surface active agents which are obtained by condensing alkylene oxides with water-soluble organic compounds containing at least six carbon atoms and having an active hydrogen, such as organic hydroxy compounds, i.e., alcohols phenols, thiophene, primary and secondary amines, carboxylic and sulfonic acids and their amides. Non-ionic polyglycol ether type surface active agents of this class are well known in the art and are disclosed, together with methods for their preparation in U.S. Pat. Nos. 1,970,578 and 2,213,477. These agents may be represented by the general formula:

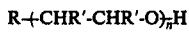

wherein R represents the residue of organic compound containing an active hydrogen and R' represents hydrogen or lower alkyl and 'n' represents an integer of from 3 to 100 or higher, but usually from 6 to 50. These compounds are readily obtained by the methods disclosed in the above cited U.S. Pat. 1,970,578 and 2,213,477 by condensing a polyglycol ether containing the required number of alkyleneoxy groups, or an alkylene oxide, usually ethylene oxide, propylene oxide or butalene oxide, with a water-insoluble organic compound containing at least 6 carbon atoms and having an active hydrogen, as for example an alkylphenol.

Other members of the group of non-ionic surfactants also may be used in this new process to prepare iodophors as for example, the class of nonionic surfactants characterized by the condensation of polyoxypropyleneglycol with ethylene oxide containing various chain lengths. Such non-ionic agents are disclosed and claimed in U.S. Pat. No. 2,674,619 and have the general formula:

wherein Y equals at least 15; and $(C_2H_4)$ $z + z'$ equals 20–90 percent of the total weight of the compound. These non-ionic surface active agents are available commercially and known by the trade name Pluronics, a product of Wyandotte chemicals Corporation of Wyandotte, Michigan and for purposes of brevity these non-ionic compounds will hereinafter be referred to as Pluronics.

A suitable non-ionic surfactant iodophor complex may be prepared by dissolving in acidified water a sufficient quantity, as for example, between 90 and 99 percent by weight of the selected non-ionic surface active agent as for example, octylphenoxypoly-(ethyleneoxy) ethanol, wherein R is an octylphenoxy group and R' is a hydrogen and n is nine, and adding from 1 to 12 grams of iodide ion obtained from a soluble iodide salt including hydriodic acid, and from 0.1 to 1.0 percent by weight of iodate ion, all the while maintaining the pH of the solution to be below pH 3. A strong brown color instantly develops as the exothermic reaction proceeds and the mixture is stirred while the pH is monitored and adding small increments of the iodate ion until there is no longer any iodide ion available upon assay. Stirring is continued for at least 1 hour, after which the solvent is evaporated.

The formed non-ionic iodophor compound obtained has a titratable iodine content ranging between 1 and 10 percent, depending upon the ratio of iodine to non-ionic agent selected. The product is distinguished in that the iodine vapor pressure is virtually eliminated so that no positive starch-iodine vapor test is obtained and the insolubility characteristic of the elemental iodine has been changed to be water soluble. The product now exhibits all of the properties for iodophors; that is, the iodine content is not extracted by chloroform and the iodine vapor pressure has been virtually eliminated. Pharmaceutical products applied to the skin may be bandaged and the aqueous solubility of iodine has been changed from the insoluble state to the soluble state. Moreover, the toxicity of elemental iodine has been markedly reduced and the formed compound despite the changes in the physical and chemical properties is superior to the older products as are known in the art. Of particular advantage of this new product when compared to those prepared by the older methods is that it is less irritating than those containing the iodide-elemental iodine contaminants and exhibits a preferred optimal superior shelf-life on aging In place of octylphenoxypoly-(ethyleneoxy) ethanol described above, there may be substituted other members of this class of non-ionic detergents as for example, nonylphenoxypoly (ethyleneoxy) ethanol.

It has also been found that iodine complexed may also be prepared utilizing members of the group of anionic surface active agents represented by the formula:

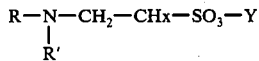

$$R-N-CH_2-CHx-SO_3-Y$$
$$|$$
$$R'$$

wherein R is the radical $CxH (2x + 1) CO$; $x$ being an integer of from 5 to 17 and R is selected from group consisting of hydrogen, ($C_1$-$C_4$) alkyl and cyclohexyl radicals and Y is selected from the group consisting of salt-forming cations. The preferred anionic detergent compounds are of the well known groups of anionic surface active agents known as alkanoyl taurates and alkylaryl sulfonates, such as alkyl benzene sodium sulfonate and alkyl naphthyl sodium sulfonate.

When it is desired to utilize anionic detergent agents as a carrier for iodine in the preparation of iodophors, then the procedure described above may be utilized wherein from 90 to 99 percent by weight of the selected anionic iodine carrier is mixed with from 1 to 10 percent by weight of iodide ion and the whole dissolved in acidulated water. Then from 0.1 to 1.0 percent of an iodate ion is added slowly until no further iodide ion is present in the solution upon testing. The solvent is evaporated to recover the formed iodophor complex in a substantially pure form.

When a cationic detergent iodophor is desired as the iodine carrier, then the well known cationic surfactant compounds as for example, the quaternary ammonium salts such as those formed by the alkylation of fatty amines; straight-chain fatty amine salts having from 8 to 18 carbon atoms in chain length, as for example, octadecyl amine; amino amides and imidazolines may be used. The manufacturing process as described above is used to result in a superior iodophor preparation than was hitherto known after the methods described in the prior art.

When a cationic detergent iodophor is to be prepared, then the same ratios of reagents are used, that is from 90 to 99 percent by weight of the selected cationic detergent compound is dissolved in a acidulated aqueous solution and from 1 to 10 percent by weight of iodide ion added together with from 0.01 to 1.0 percent of iodate ion. The mixture is stirred until no iodide ion is evident upon testing. The formed cationic detergent iodophor is recovered in a substantially pure form and exhibits an extraordinary stability.

It is well known that iodide ions are necessary to achieve the solubility of iodine and that iodide ions are essential to the formation of non-ionic and anionic iodophor preparations, although it has been claimed that cationic iodophor preparations are not depedent upon the level of iodide ions. It is just this very property of iodide ions that results in some of the problems observed with iodophor preparations which affect their toxicity and stability. Moreover, iodophor compounds, when dissolved in water, give rise to a certain concentration of iodide ion which acts as an autocatalyst to further degrade the compound upon aging. Thus the United States Pharmacopeia establishes a limit for iodide concentration for its official iodophor to be not more than 6.6% and even this is considered high. The iodide content of some iodine preparations remains as high as 10 to 15% and even higher because of the conversion of the titratable iodine level to hydrioc acid by interaction with the solvent and then conversion to iodide salts by reaction with metallic components therein.

Thus, irrespective of the method of manufacture of the iodophor compounds, even those compounds which as a raw material may be little or more iodide ions present as a contaminant. When a pharmaceutical dose is being prepared a certain level of iodide ions are formed and this aids to degrade the compound on aging.

It was found that by adding 0.1 to 1.0 percent by weight of iodate ions at the time of manufacture of pharmaceutical dosage forms containing iodophor compounds, that the instability characteristic imported by the iodide ion may be neutralized so that there is no marked drop in titratable iodine content after measure of these dosage forms. This procedure results in a lower cost of manufacture because the addition of an excess amount of iodophor ingredient to compensate for the drop in available iodine due to auto-degradation of the iodophor compound is now avoided and the resultant preparations possess more uniform, reproducible as well as constant level of titratable iodine and antimicrobial potency than the commercially available product.

It was unexpectedly found that this property of enhancing the stability and potency of the iodophor compounds could be obtained without the need of an acid pH to the pharmaceutical dosage form so that preparations intended to be used on open wounds may be protected in this manner.

In operation, the proper amount of iodate ion added to the pharmaceutical iodophor preparation, is accomplished at the time of addition of the iodophor active ingredient so that iodide ion present in the active ingredient is immediately neutralized and formation of further iodide ion is avoided. The addition of the iodate ion may be made immediately before; simultaneously with or immediately after the addition of the active iodophor compound in the course of manufacture.

A useful guide to the amount of iodate ion to be added is one part by weight of iodate ion ($IO_3^-$) for every five parts by weight of iodide ion. While this guide is useful to calculate the amount of reagents necessary, as with all large-scale manufacturing procedures, these ratios are general. It is preferred that the amount of iodate ion to be added to a sufficient quantity ion, is determined upon assay.

For purposes of understanding the present invention, the essential embodiment discussed herein has been the iodate ion. It was further found that other substances could be utilized in the same manner as set forth above, to accomplish the same result. The common property essential for all of these other groups is their ability to serve as an oxidizing stabilizer compound. Thus, non-limiting examples of alternative agents which may be utilized as a stabilizing compound in the process of the present invention are:

(a) Bromate ion ($BrO_3^-$), which is used preferably in a ratio of one molar fraction of bromate ion for every six molar fractions of iodide ion present.

(b) Chlorite ion ($ClO_2^-$), which is used preferably in a ratio of one molar fraction of chlorite ion for every four molar fractions of iodide ion present.

(c) Chromate ion ($Cr_2O_7^-$), which is used preferably in a ratio of one molar fraction of cromate ion for every six molar fractions of iodide ion present.

(d) Hydrogen Peroxide is used in a preferred amount of one gram molecular weight of hydrogen peroxide for every two molar fractions of iodide ion present.

(e) Hypochlorite ion ($OCl^-$), which is used preferably in a ratio of one molar fraction of hypochlorite ion for every two molar fractions of iodide ion present.

(f) Nitrite ion ($NO_2$), which is used in a preferred amount of one gram molecular fraction of nitrite ion for every molecular fraction of iodide ion present.

(g) Permanganate ion ($MnO_4^=$), which is used preferably in a ratio of one molar fraction of permanganate ion for every five molar fractions (h) Persulfate ion ($S_2O_8^=$), which is used in the ratio of one molar fraction of persulfate ion for every two molar fractions of iodide ion present.

When using the aforesaid alternate stabilizer compounds either to manufacture an iodophor compound or for the stabilization of an iodophor-containing pharmaceutical dosage form, in accord with the methods described above and in the general proportions disclosed, the addition of the selected stabilizing agent is preferably added slowly, with testing for iodide content, until there is no further iodide ion determined.

It is recognized that the stabilizing ions described herein are derived from an alkaline salt of the kind which may yield such ions, as for example, potassium, sodium, lithium, magnesium, calcium, ammonium and other like metallic iodate salts, will be found useful, to release the respective reagent ion during the iodophor manufacturing process. While it is not necessary for virtually all of ordinary uses of iodophor compounds to remove the small amount of metallic ion remaining, this step of further purification may be readily accomplished by simple dialysis with distilled water, if desired, since the soluble metallic ions will pass through the conventional semi-permeable membranes used in dialysis purification techniques but the formed iodophor compound because of its large molecular weight, will not dialyze and remain in solution.

Reference has been made to acidulated aqueous and-/or aqueous-organic solvents for the manufacture of the active iodophor compound or for the stabilization of the respective dosage form containing said iodophor compound. Such a solvent must be a polar or semi-polar solvent, as for example, water, the liquid alcohols as for example, methanol, ethanol, propanol, isopropyl, butanol, isobutyl alcohol and other liquid alsohols up to and including those alcohols having a carbon chain length of 10, and acetone. Glycerin, propylene glycol and the liquid polyoxyethylene glycols also may be utilized as solvents for the present processes. The different organic polar solvents such as are well known to the art also have utility in carrying out specific purposes, although it will be found that they may be somewhat costly. The exact amount of water, or aqueous-polar solvent necessary for the present invention to take place is a minimal quantity. Generally the amount should be just sufficient for the iodide ion to be soluble therein and for the reagent stabilizing ion to act thereon. It was found that quantities of water and other polar solvents as low as one percent by weight of iodophor reagents used was sufficient to obtain a positive result.

The following examples serve to illustrate our invention but it is not intended to be limited thereby.

EXAMPLE 1

In a suitable glass container fitted with a stirrer and an inlet tube is added a solution of 10 grams of polyvinylpyrrolidone (povidone) having an average molecular weight of 40,000 dissolved in 50 ml. of acidulated distilled water (pH below pH 4). The stirring is started and one gram of potassium iodide is added. When the potassium iodide has dissolved, a solution of 0.1 molar potassium iodate is added in small increments. Gnerally about 1 gram of potassium iodate will be required to completely eliminate the iodide ion present to form polyvinylpyrrolidone-iodine. The stirring is continued until no further positive test for iodide ion is obtained.

Upon the addition of the iodate ion an immediate brown coloration appears which deepens as additional iodate ion is added and the reaction progresses in time. After about one hour stirring at room temperature, the reaction has stabilized so that the stirring may be stopped and the whole set aside overnight. The solvent is then recovered by evaporation under vacuum and the formed povidone-iodine recovered. The formed povidone-iodine is a reddish-brown, free-flowing powder containing 9.95 percent of available iodine as determined by thiosulfate titratable and its Kjeldahl nitrogen analysis is 10.1 percent. The ash content is 0.01 percent and iodide content is nil.

Povidone-iodine thus formed, is completely soluble in water, ethyl alcohol, and acetone. It is insoluble in tetrahydrofuran, ethyl acetate, hexane and carbon tetrachloride. When treated with dioxane, the formed polyvinylpyrrolidone swells but does not dissolve. The vapor pressure of the formed polyvinylpyrrolidone-iodine is less than 0.01 at 50° C. and it does not give a positive starch-iodine test for iodine vapor.

Polyvinylpyrrolidone-iodine obtained as described above may be stored for prolonged periods in the dry form in stoppered containers without loss of iodine, even at elevated temperatures.

The formed polyvinylpyrrolidone-iodine is virtually non-toxic and non-corrosive to humand and animal skin and kills on contact bacteria, viruses, fungi, protozoa and yeast. It is sporicidal and its activity antimicrobial spectrum parallels that of the commercially available povidone-iodine.

EXAMPLE 2

In place of the povidone used in Example 1 above, which has an average molecular weight of 40,000 there may be used any other polyvinylpyrrolidone polymer which ranges in molecular weight of from 10,000 to 700,000. The remainder of the steps being the same; the difference in the properties of the formed povidone-iodine iosophor reside in its solubility characteristics in an aqueous solvent rather than in its antimicrobial spectrum. The more insoluble the compound, the longer it will take to achieve an equivalent antimicrobial action.

EXAMPLE 3

An alternate procedure to prepare polyvinylpyrrolidone virtually free of iodide ion is to combine 90 parts by weight of povidone having a molecular weight of between 10,000 and 700,000, such as is described in the U.S.P. XIX, p. 395, with 10 gm. of elemental iodine, and 0.4 gm. of potassium iodate. The mixture is intimately ground in a ball-mill for approximately four hours or tumbled in a conventional mixer for a period of 12 hours. The resultant powder when dissolved in water, provides essentially 10 percent by weight of titratable iodine with less than 1 percent iodide content. It behaves in all other respects as povidone-iodine, known to the art, except that it does not show the initial drop in titratable iodine upon dissolution in aqueous solvents as is known for the older product.

The above process for preparing povidone-iodine may also be carried out in solution whereupon 90 parts by weight of povidone is dissolved in 50 ml. of distilled water and 10 gm. elemental iodine is added with stirring. Potassium iodate in 0.1 gm. increment is added immediately after each addition of elemental iodine.

The solution is tested periodically to determine the absence of iodide ion. When the reaction is complete as evidenced by the absence of iodide ions, an additional 0.1 gm. of potassium iodate is added and the whole set aside overnight. The resultant solution contains povidone-iodine which meets all of the requirements of U.S.P. XIX, p. 395. The formed povidone-iodine may be recovered by vacuum distillation of the solvent, if desired.

EXAMPLE 4

Polyvinylpyrrolidone-iodine compounds containing from 1 percent to 30 percent by weight of available or titratable iodine may be prepared in the manner described above by suitable adjustment of the ratio of reagents to be used. The preferred ratio of iodate ion to iodide ion is 1 gm. molecular weight fraction of iodate ion for each 5 gm. molecular weight fractions of iodide ion used and 0.04 percent by weight of iodate ion for each percent by weight of elemental iodine used. The remainder of the steps are the same.

EXAMPLE 5

When it is desired to prepare a non-ionic surfactant iodophor compound, then 50 gm. of a non-ionic detergent compound, defined herein above as Pluronics, manufactured by Wyandotte Chemicals Corporation of Wyandotte, Mich., and which are disclosed in U.S. Pat. No. 2,674,619, dated Apr. 6, 1954, is dissolved in 250 ml. of water, made acid to pH 3, and to this is added 20 gm. of potassium iodide and the pH again adjusted to be less than pH 3. The mixture is stirred until complete solution is achieved and 2 gm. of potassium iodate are added in small increments until no iodide ion remains The mixture is stirred for four hours and set aside overnight. The next day the solvent is removed and the formed non-ionic pluronic-iodine compound is obtained, which corresponds chemically to the compound Poly(oxyethelene)-poly(oxypropylene)poly(oxyethylene)-iodine having 23 percent available iodine by titration. The non-ionic detergent iodophor formed is soluble in water and possesses the full spectrum of antimicrobial properties that is known for elemental iodine but without its high vapor pressure or corrosive properties to tissue.

Any member of the pluronic group of non-ionic polyol detergent compound may be substituted in equal quantities as described above to obtain the respective iodophor compounds. Such pluronic polyols are commercially available from BASF, Wyandotte Corporation in Wyandotte, Mich. and described in the above-noted U.S. Pat. No. 2,674,619.

EXAMPLE 6

In place of the pluronics noted above there may be substituted equimolar quantities, therefore a non-ionic detergent polyglycol ether compound having the general formula:

whereupon R represents the residue of organic compound containing an active hydrogen and R' represents hydrogen or lower alkyl and $n$ represents an integer of from 3 to 100 or higher, but usually from 6 to 50. These compounds are readily obtained by the methods disclosed in the above cited U.S. Pat. 1,970,578 and 2,213,477 by condensing a polyglycol ether containing the required number of alkyleneoxy groups, or an alkylene oxide, usually ethylene oxide, propylene oxide or butylene oxide, with a water-insoluble organic compound containing at least 6 carbon atoms and having an active hydrogen, as for example an alkylphenol.

A suitable example of a member of this class of compounds is octylphenoxypoly-(ethyleneoxy) ethanol, wherein R is an octylphenoxy group and R' is a hydrogen and $n$ is nine.

In a suitable glass container is placed 9.9 gm. of octylphenoxypoly(ethyleneoxy) ethanol, dissolved in 50 ml. of water to which is added 0.1 gm. of potassium iodide. The mixture is then acid to a pH of below 3 and 0.02 gm. of iodate ion added with stirring. After standing for twenty-four hours, the solvent is evaporated under vacuum and the formed octylphenoxypoly-(ethyleneoxy)ethanol-iodine is obtained in substantially pure form, without iodide ions.

Other members of this class of non-ionic detergents may be used in equimolar proportions, should it be desired to obtain a different iodophor compound.

EXAMPLE 7

When an anionic detergent is intended to be used to prepare an iodophor compound, then the oleic acid ester of sodium isethionate, 10 parts, is dissolved in 50cc. of water and 1 part of hydriodic acid dissolved in 10cc. of water is added to it. The mixture is stirred and 0.1 part of potassium iodate is added whereupon the solution turns dark brown. The mixture is set aside overnight and the solvent is removed under vacuum.

The formed iodophor compound is germicidally active and useful to prepare pharmaceutical dosage forms. It is stable in solution as well as in the isolated state.

In place of the oleic acid ester of sodium isethionate described above, there may be substituted in equimolar quantities, coconut acid ester of sodium isethioate, sodium N-methyl-N-oleoyl taurate, sodium N-methyl-N-"coconut oil acid" taurate, sodium N-methyl-N-"tall oil acid" taurate, sodium N-cyclohexyl-N-palmitoyl taurate, sodium N-methyl-N-palmitoyl taurate, sodium N-methyl-N-"tallow acid" taurate to form the corresponding iodophor compound.

EXAMPLE 8

When a cationic detergent iodophor product is desired, then 90 parts by weight of octadecylamine is dissolved in 500 ml. of water which is acidified to pH 2. Twelve parts by weight of iodide ion as provided by potassium iodide, is added together with 0.5 percent of potassium iodate ion. The pH is carefully adjusted to be no greater than pH 3. The mixture is stirred and tested for the presence of iodide ion and when the test for iodide ion is no longer positive the formed octadecylamine-iodine iodophor compound may be isolated therefrom. The product is a germicidal compound useful in sanitizing inanimate surfaces against microbial contamination.

EXAMPLE 9

In place of the potassium iodide described above, there may be substituted equimolar quantities, an iodide salt soluble in the selected reaction solvent, such salts as sodium iodide, lithium iodide, calcium iodide, and magnesium iodide as well as hydriodic acid ($HI^-$) are particularly useful.

EXAMPLE 10

In place of the potassium iodate or iodate ion described above, there may be substituted in equimolar proportions by weight an alternate stabilizer compound such as the bromate ion, chlorite ion, chromate ion, hydrogen peroxide, hypochlorite ion, nitrate ion, permanganate ion and persulfate ion. When these agents are used the amounts preferred are:

(a) Bromate Ion ($BrO^-_3$) which is used preferably in a ratio of one molar fraction of bromate ion for every six molar fractions of iodide ion present.
(b) Chlorite Ion ($ClO^-_2$) which is used preferably in a ratio of one molar fraction of chlorite ion for every four molar fractions of iodide ion present.
(c) Chromate ion ($Cr_2O_7^-$) which is used preferably in a ratio of one molar fraction of cromate ion for every six molar fractions of iodide ion present.
(d) Hydrogen Peroxide is used in a preferred amount of one gram molecular weight of hydrogen peroxide for every two molar fractions of iodide ion present.
(e) Hypochlorite Ion ($OCl^-$) which is used preferably in a ratio of one molar fraction of hypochlorite ion for every two molar fractions of iodide ion present.
(f) Nitrate Ion ($NO_2$) which is used in a preferred amount of one gram molar fraction of nitrate ion for every molecular fraction of iodide ion present.
(g) Permanganate Ion ($MnO_4^-$) which is used preferably in a ratio of one molar fraction of permanganate ion for every five molar fractions of iodide ion present.
(h) Persulfate Ion ($S_2O_8^-$) which is used in the ratio of one molar fraction of persulfate ion for every two molar fractions of iodide ion present.

The remainder of the steps being the same.

EXAMPLE 11

When it is desired to eliminate contaminant iodide ions and to suppress and/or avoid the formation of iodide ion in the course of the manufacture of a pharmaceutical iodophor dosage form, then from 0.001 to 1.0 percent by weight of an iodate compound as for example, potassium iodate, in added to the composition at or about the time of the addition of the iodophor compound. Thus, if povidone-iodine solution were to be prepared in accord to meet the United States Pharmacopeia XIX requirements, then from 0.005 to 0.15 percent of potassium iodate would be added to each 10 gm. of povidone-iodine, depending on the concentration of iodides present. It is to be noted that the U.S.P. XIX limit on iodide content is not more than 6.6 percent. This ratio of iodide ion concentration in the active iodophor compound pertains to any pharmaceutical dosage form containing povidone-iodine as the iodate, whether it be povidone-iodine ointment, povidone-iodine shampoo, povidone-iodine douche, povidone-iodine scrub, povidone-iodine mouthwash gargle, and other povidone-iodine containing pharmaceutical dosage forms.

What is claimed is:

1. A method of producing an organic iodophor germicidal composition which is substantially free of iodide contamination and therefore non corrosive, which comprises reacting an organic iodophor-forming compound with an iodine adding agent selected from the group consisting of elemental iodine, metallic iodide salts capable of releasing iodide ion, and hydriodic acid in the presence of 0.005–1% by weight of an oxidizing stabilizer selected from the group consisting of iodate ions, bromate ions, chlorite ions, chromate ions, hypochlorite ions, nitrate ions, permanganate ions, persulfate ions, and hydrogen peroxide, whereby iodine adds to said organic iodophor-forming compound to form the corresponding organic iodophor which is free of iodide ions and therefore non-corrosive.

2. The method according to claim 1 wherein said organic iodophor-forming compound is povidone.

3. The method according to claim 1, wherein said organic iodophor-forming compound is a nonionic surface active agent.

4. The method according to claim 1 wherein said organic iodophor-forming compound is octylphenoxypoly-(ethyleneoxy) ethanol.

5. The method according to claim 1 wherein said organic iodophor-forming compound is nonylphenoxypoly (ethyleneoxy) ethanol.

6. The method according to claim 1 wherein said organic iodophor-forming compound is the condensation product of polyoxypropyleneglycol with ethylene oxide.

7. The method according to claim 1 wherein said organic iodophor-forming compound is an anionic surface active agent.

8. The method according to claim 1 wherein said organic iodophor-forming compound is an alkylaryl sulfonate.

9. The method according to claim 1 wherein said organic iodophor-forming compound is a cationic detergent selected from the group consisting of quaternary ammonium salts, straight chain fatty amine salts having 8 to 18 carbon chain lengths, amino-amides and imidazolines.

10. The method according to claim 1 wherein said iodine adding agent is a metallic iodide salt selected from the group consisting of potassium iodide, sodium iodide, lithium iodide, calcium iodide, mangesium iodide and ammonium iodide.

11. The method according to claim 1 wherein said oxidizing stabilizer is potassium iodate.

12. The method according to claim 1 wherein said oxidizing stabilizer is ammonium persulfate.

13. The pharmaceutical iodophor germicidal composition produced by the method of claim 1.

14. The method of eliminating unreacted iodine and iodide contaminants from an iodophor germicidal composition which comprises adding thereto from 0.001 percent to 1.0 percent by weight of an ion selected from the group consisting of iodate ions, bromate ions, chlorite ions, chromate ions, hypochlorite ions, nitrate ions, permanganate ions, persulfate ions and hydrogen peroxide.

* * * * *